(12) United States Patent
Igarashi

(10) Patent No.: US 9,761,048 B2
(45) Date of Patent: Sep. 12, 2017

(54) MEDICAL IMAGE PROCESSING APPARATUS AND MEDICAL IMAGE PROCESSING METHOD

(71) Applicant: TOSHIBA MEDICAL SYSTEMS CORPORATION, Otawara-Shi (JP)

(72) Inventor: Takuma Igarashi, Nasushiobara (JP)

(73) Assignee: Toshiba Medical Systems Corporation, Otawara-Shi (JP)

( * ) Notice: Subject to any disclaimer, the term of this patent is extended or adjusted under 35 U.S.C. 154(b) by 113 days.

(21) Appl. No.: 14/953,879

(22) Filed: Nov. 30, 2015

(65) Prior Publication Data
US 2016/0078677 A1    Mar. 17, 2016

Related U.S. Application Data

(63) Continuation of application No. PCT/JP2014/064819, filed on Jun. 4, 2014.

(30) Foreign Application Priority Data

Jun. 7, 2013   (JP) .................................. 2013-121062

(51) Int. Cl.
| | |
|---|---|
| G06K 9/00 | (2006.01) |
| G06T 19/00 | (2011.01) |
| A61B 6/03 | (2006.01) |
| A61B 6/00 | (2006.01) |
| A61B 8/08 | (2006.01) |

(Continued)

(52) U.S. Cl.
CPC .............. *G06T 19/00* (2013.01); *A61B 6/032* (2013.01); *A61B 6/504* (2013.01); *A61B 6/5217* (2013.01);
(Continued)

(58) Field of Classification Search
None
See application file for complete search history.

(56) References Cited

U.S. PATENT DOCUMENTS

| | | |
|---|---|---|
| 2005/0090743 A1 | 4/2005 | Kawashima et al. |
| 2006/0056681 A1* | 3/2006 | Matsumoto ........... G06T 11/008 |
| | | 382/154 |

(Continued)

FOREIGN PATENT DOCUMENTS

| | | |
|---|---|---|
| JP | 5-266214 | 10/1993 |
| JP | 2001-14495 | 1/2001 |

(Continued)

OTHER PUBLICATIONS

International Search Report issued Jul. 1, 2014 in PCT/JP2014/064819, filed Jun. 4, 2014 (with English Translation).

(Continued)

*Primary Examiner* — Amara Abdi
(74) *Attorney, Agent, or Firm* — Oblon, McClelland, Maier & Neustadt, L.L.P.

(57) ABSTRACT

According to one embodiment, a medical image processing apparatus includes processing circuitry. The processing circuitry extracts a core line of a tubular structure from three dimensional medical image data. For each section of interest of a plurality of sections of interest, the section of interest crossing the core line, being a tubular cross-section of the tubular structure, and including a portion of interest, the processing circuitry sets a straight line in the section of interest crossing the core line and passing through the portion of interest included in the section of interest as a first cut-off line. Further, the processing circuitry sets a curved plane such that the curved plane passes through a plurality of first cut-off lines being set in the corresponding plurality of sections of interest, and the processing circuitry generates a reconstruction image along the set curved plane.

10 Claims, 13 Drawing Sheets

(51) Int. Cl.
    *G06T 7/00*         (2017.01)
    *G06T 15/00*        (2011.01)
    *G06T 15/08*        (2011.01)
    *A61B 5/055*            (2006.01)
    *A61B 5/00*             (2006.01)
    *A61B 34/10*            (2016.01)

(52) U.S. Cl.
    CPC ............ *A61B 6/5223* (2013.01); *A61B 8/523* (2013.01); *A61B 8/5207* (2013.01); *G06T 7/0012* (2013.01); *G06T 15/005* (2013.01); *G06T 15/08* (2013.01); *A61B 5/055* (2013.01); *A61B 5/489* (2013.01); *A61B 2034/104* (2016.02); *A61B 2034/105* (2016.02); *A61B 2576/02* (2013.01); *G06T 2200/04* (2013.01); *G06T 2207/10072* (2013.01); *G06T 2207/10116* (2013.01); *G06T 2207/30101* (2013.01); *G06T 2210/41* (2013.01); *G06T 2215/06* (2013.01); *G06T 2219/008* (2013.01)

(56) References Cited

U.S. PATENT DOCUMENTS

| | | | | |
|---|---|---|---|---|
| 2010/0008557 A1* | 1/2010 | Matsumoto | ........ | G06K 9/00208 382/131 |
| 2010/0092053 A1* | 4/2010 | Manabe | ............... | G06K 9/4638 382/128 |
| 2010/0215225 A1* | 8/2010 | Kadomura | ............ | G06T 7/0012 382/128 |
| 2012/0026162 A1* | 2/2012 | Masumoto | .............. | G06T 19/00 345/419 |
| 2012/0093388 A1* | 4/2012 | Masumoto | ............ | G06T 7/0012 382/134 |

FOREIGN PATENT DOCUMENTS

| | | |
|---|---|---|
| JP | 2005-118162 | 5/2005 |
| JP | 2006-51154 | 2/2006 |
| JP | 2006-75216 | 3/2006 |
| JP | 2010-17474 | 1/2010 |
| JP | 2012-24517 | 2/2012 |
| JP | 2013-52121 | 3/2013 |
| WO | WO 2006/118100 A1 | 11/2006 |

OTHER PUBLICATIONS

International Preliminary Report on Patentability and Written Opinion issued Dec. 17, 2015 in PCT/JP2014/064819 filed Jun. 4, 2014 (submitting English translation only).

* cited by examiner

MEDICAL IMAGE PROCESSING APPARATUS AND MEDICAL IMAGE PROCESSING METHOD

CROSS-REFERENCE TO RELATED APPLICATIONS

This application is a Continuation Application of No. PCT/JP2014/64819, filed on Jun. 4, 2014, and the PCT application is based upon and claims the benefit of priority from Japanese Patent Application No. 2013-121062, filed on Jun. 7, 2013, the entire contents of which are incorporated herein by reference.

FIELD

Embodiments described herein relate generally to a medical image processing apparatus and a medical image processing method.

BACKGROUND

As a method of observing a tubular structure on the basis of volume data (medical 3D image data) obtained by an X-ray CT (Computed Tomography) device, a magnetic resonance imaging device (hereinafter referred to as an MRI device) and the like, an MPR (Multi-Planner Reconstruction) method, a curved multi-planner reconstruction (CPR) method, and a stretched CPR method (hereinafter referred to as an SPR method) are known.

The MPR method is a method in which 3D data is cut off on a plane in an arbitrary direction and a sectional image seen from a direction perpendicular to this plane is reconstructed. On the other hand, the CPR method is a method mainly used when a tubular structure in the 3D image data is to be observed, in which the 3D image data is cut off along a core line of the tubular structure and the sectional image along the core line of the tubular structure is reconstructed by projecting this curved plane to a predetermined projection plane. The SPR method is a method of further stretching the core line extracted by the CPR method linearly. According to these methods, a user can easily observe the section of the tubular structure.

However, these sectional images are only images of one section of a tubular structure. The sectional image obtained by the CPR method, for example (hereinafter referred to as a CPR image) has only information which can be caught on a specific section along the core line of the tubular structure, and images of a portion of interest such as stricture or hypertrophy present at a position dislocated in a depth direction with respect to this section cannot be included. Therefore, when the user observes the CPR image, it is extremely difficult to discover the portion of interest not included in the CPR image.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of a medical image processing apparatus and a medical image processing method according to embodiments of the present invention with reference to the drawings.

In general, according to one embodiment, a medical image processing apparatus includes processing circuitry. The processing circuitry extracts a core line of a tubular structure from three dimensional medical image data. For each section of interest of a plurality of sections of interest, the section of interest crossing the core line, being a tubular cross-section of the tubular structure, and including a portion of interest, the processing circuitry sets a straight line in the section of interest crossing the core line and passing through the portion of interest included in the section of interest as a first cut-off line. Further, the processing circuitry sets a curved plane such that the curved plane passes through a plurality of first cut-off lines being set in the corresponding plurality of sections of interest, and the processing circuitry generates a reconstruction image along the set curved plane.

Figure 1:
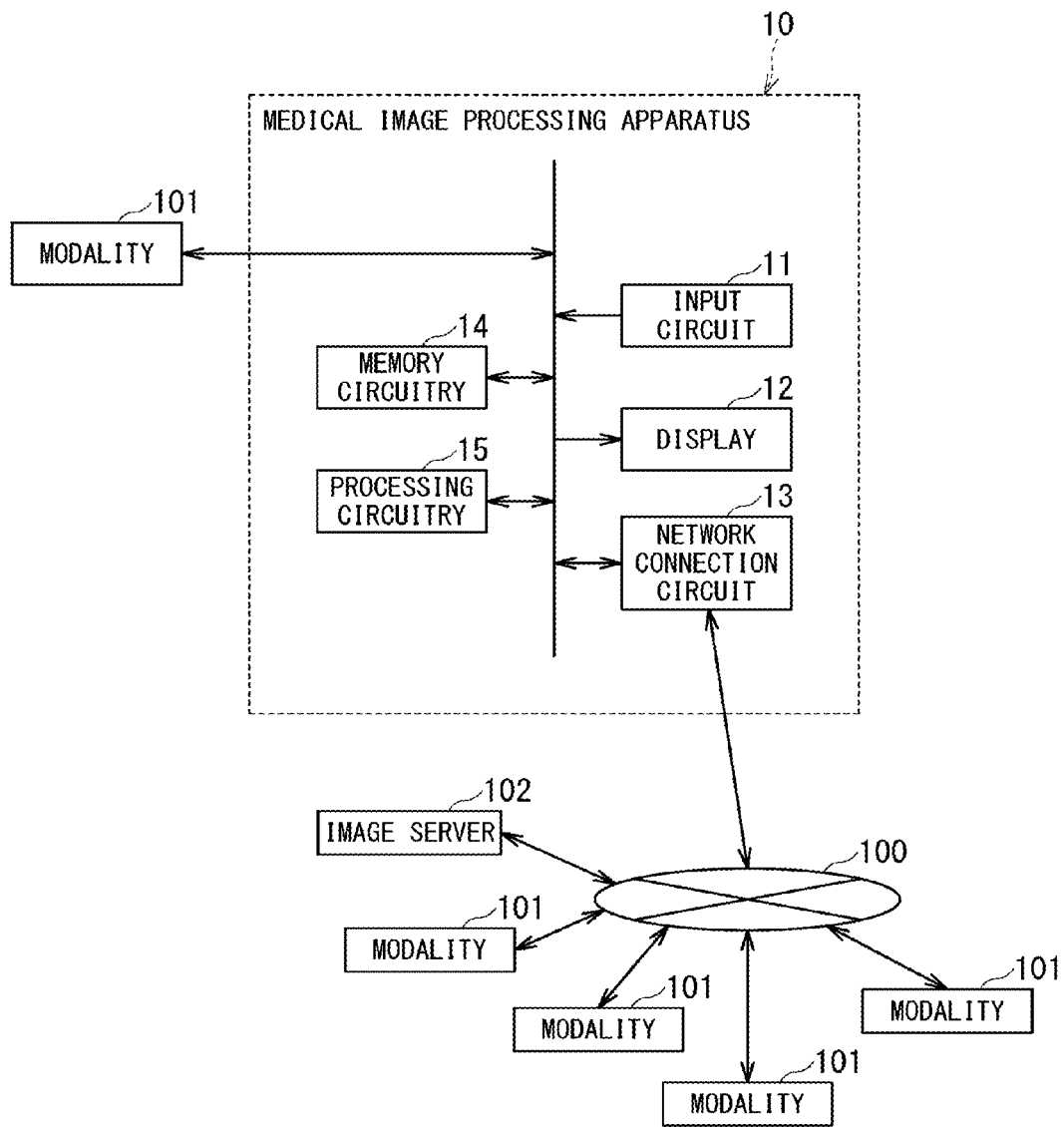
FIG. 1 is a block diagram illustrating a constitution example of a medical image processing apparatus according to an embodiment of the present invention.

FIG. 1 is a block diagram illustrating a constitution example of a medical image processing apparatus 10 according to an embodiment of the present invention.

The medical image processing apparatus 10 has an input circuit 11, a display 12, a network connection circuit 13, memory circuitry 14, and processing circuitry 15 as illustrated in FIG. 1.

The input circuit 11 includes at least a pointing device and is constituted by general input devices such as a mouse, a track ball, a keyboard, a touch panel, a ten key and the like, for example, and outputs an operation input signal corresponding to an operation by a user to the processing circuitry 15.

The display 12 is constituted by general display output devices such as a liquid crystal display and an OLED (Organic Light Emitting Diode) display, for example, and displays various images such as a medical image in accordance with control of the processing circuitry 15.

The network connection circuit 13 implements various protocols for information communication according to a mode of a network 100. The network connection circuit 13 connects the medical image processing apparatus 10 to other electric devices in accordance with the various protocols. Here, the network 100 means an information communication network in general using a telecommunication technology and includes a wireless/wired LAN such as a hospital backbone LAN (Local Area Network) and an internet network, a telephone communication line network, an optical fiber communication network, a cable communication network, a satellite communication network and the like.

The memory circuitry 14 stores medical volume data (three dimensional medical image data, hereinafter referred to as medical 3D image data) output from a modality 101 and reconstruction image data. The modality 101 is a medical image diagnosis device such as an X-ray CT (Computed Tomography)device, an MRI (Magnetic Resonance Imaging) device, an ultrasonic diagnosis device, and an X-ray diagnosis device and can be constituted by devices capable of generating volume data (3D image data) on the basis of projection data obtained by photographing of an object (patient).

Moreover, the medical image processing apparatus 10 may receive a reconstruction image or volume data from the modality 101 or an image server 102 connected via the network 100. The reconstruction image or volume data received via the network 100 is also stored in the memory circuitry 14. Moreover, the medical image processing apparatus 10 may be included in the modality 101 as a constituent element of the modality 101.

The image server 102 is a server for long-term storage of an image provided in a PACS (Picture Archiving and Communication System), for example, and stores the reconstruction image or volume data generated in the modality 101 such as the X-ray CT (Computed Tomography) device, the magnetic resonance imaging (MRI) device, and the ultrasonic diagnosis device connected via the network 100.

The processing circuitry 15 has at least a processor and is constituted by the processor and a recording medium including a RAM, and a ROM, for example, and controls an operation of the medical image processing apparatus 10 in accordance with a program stored in this storage medium.

The processor of the processing circuitry 15 loads a medical image processing program stored in the recording medium including the ROM and data required for executing this program to the RAM and executes processing for generating a twisted curved multi-planner reconstruction image (tCPR image) including more images of portions of interest in accordance with this program.

The RAM of the processing circuitry 15 provides a work area for temporarily storing a program executed by the processor and data. The storage medium including the ROM of the processing circuitry 15 stores a start-up program of the medical image processing apparatus 10, a medical image processing program and various types of data required for executing these programs. The recording medium including the ROM has a constitution including a recording medium such as a magnetic or optical recording medium or a semiconductor memory that can be read by the processor and may be constituted such that a part of or the whole of the programs and data in the recording medium can be downloaded via an electronic network.

Figure 2:
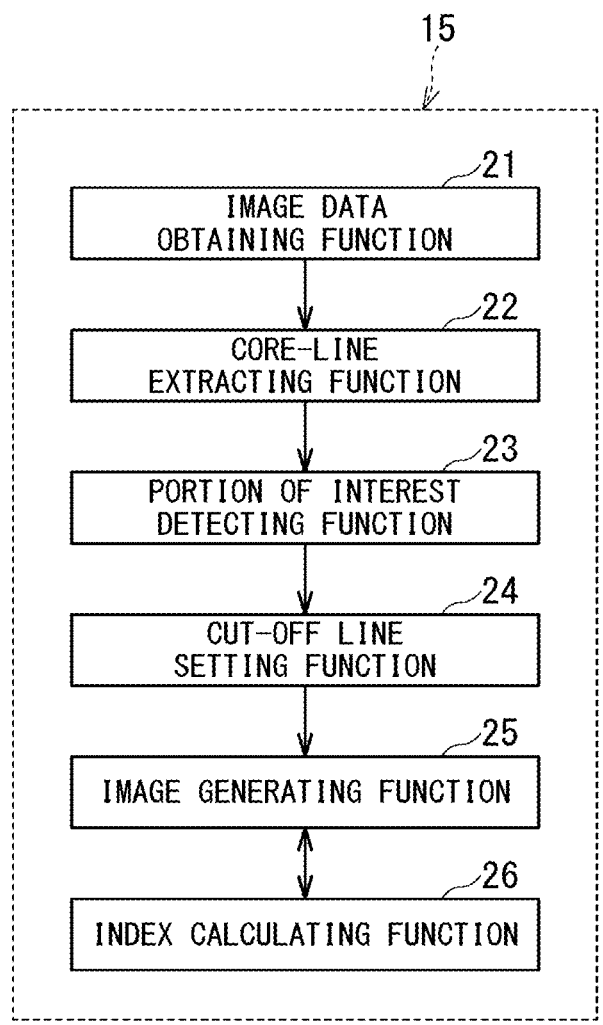
FIG. 2 is a schematic block diagram illustrating an example of functions to be realized by the processor of the processing circuitry.

FIG. 2 is a schematic block diagram illustrating an example of functions to be realized by the processor of the processing circuitry 15.

As illustrated in FIG. 2, the processor of the processing circuitry 15 functions at least as an image data obtaining function 21, a core-line extracting function 22, a portion of interest detecting function 23, a cut-off line setting function 24, an image generating function 25, and an index calculating function 26 by a medical image processing program. Each of these functions is stored in the memory circuitry in a form of a program, respectively.

The image data obtaining function 21 obtains at least volume data generated by the modality 101 and stores it in the memory circuitry 14.

Here, a prior-art CPR image will be described in brief.

Figure 3:
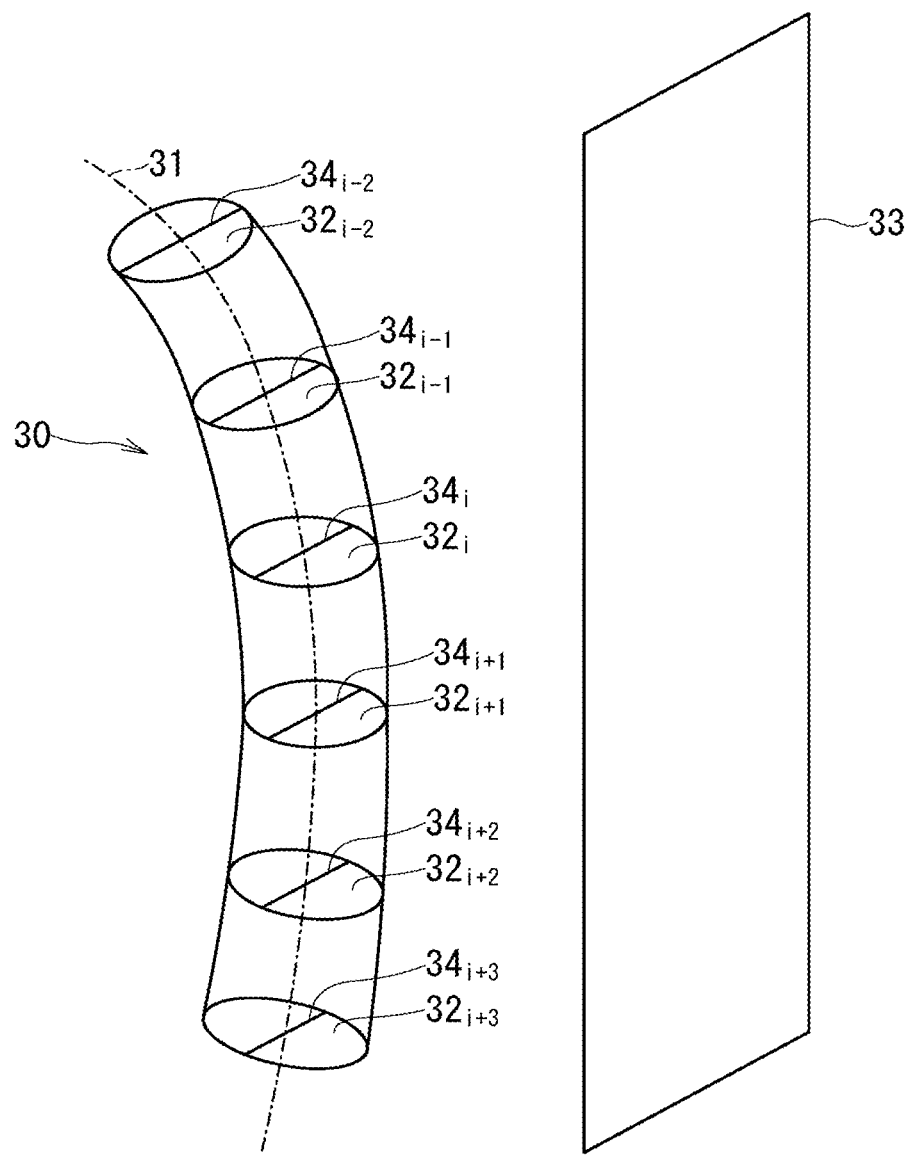
FIG. 3 is an explanatory view illustrating an example of a prior-art generating method of a CPR image.

FIG. 3 is an explanatory view illustrating an example of a prior-art generating method of a CPR image.

As illustrated in FIG. 3, when the prior-art CPR image is to be generated, first, a plurality of tubular cross-sections $32_i$ (i is a positive integer) crossing (or substantially orthogonal to, for example) a core line 31 of a tubular structure 30 including a blood vessel such as a coronary artery, a bronchus, a large intestine, a small intestine and the like are set on the basis of volume data. Then, for each of the plurality of tubular cross-sections $32_i$, cut-off lines $34_i$ which are straight lines in the tubular cross-sections $32_i$ parallel with a predetermined projection plane 33 and passing through a center of this tubular cross-section $32_i$ are set. Then, data belonging to this cut-off line $34_i$ is extracted from the volume data, and by projecting data of the plurality of cut-off lines $34_i$ to the projection plane 33, the prior-art CPR image is generated.

Thus, all the cut-off lines $34_i$ are in parallel with the projection plane 33. In other words, rotation angles around the core line 31 based on a direction in the tubular cross-section $32_i$ in parallel with the projection plane 33 and crossing the core line 31 are fixed and become same with respect to all the cut-off lines $34_i$. Therefore, in an example illustrated in FIG. 3, for example, each of the cut-off lines $34_{i-2}, 34_{i-1}, \ldots 34_{i+3}$ is in parallel with each other.

Figure 4:
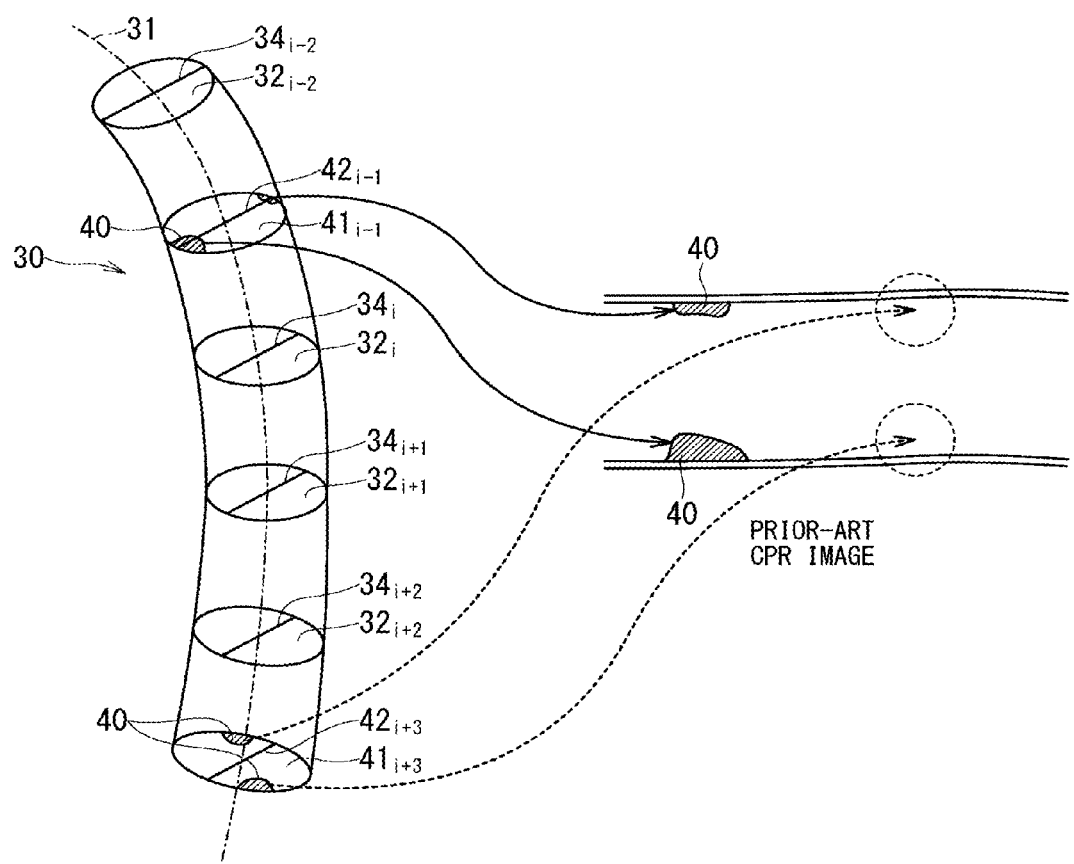
FIG. 4 is an explanatory view illustrating an example of a relation between the prior-art CPR image and the cut-off line.

FIG. 4 is an explanatory view illustrating an example of a relation between the prior-art CPR image and the cut-off line 34. FIG. 4 is a view further illustrating an example in which the tubular cross-section $32_{i-1}$ and $32_{i+3}$ are sections (hereinafter referred to as sections of interest) 41 including a point which should draw attention by other users (hereinafter referred to as a portion of interest) 40 such as an abnormal spot including a stricture or hypertrophy in the example illustrated in FIG. 3.

The cut-off line $34_{i-1}$ of the section of interest $41_{i-1}$ is a straight line (hereinafter referred to as a first cut-off line) $42_{i-1}$ passing through the portion of interest 40 included in this section of interest $41_{i-1}$ and also passing through a center of the section of interest $41_{i-1}$. Thus, information of the portion of interest 40 included in the section of interest $41_{i-1}$ caught by this first cut-off line $42_{i-1}$ is reflected in the prior-art CPR image and can be visually recognized by the user (see a right view in FIG. 4).

On the other hand, the cut-off line $34_{i+3}$ of the section of interest $41_{i+3}$ does not pass through the portion of interest 40 included in this section of interest $41_{i+3}$. Thus, the information of the portion of interest 40 included in this section of interest $41_{i+3}$ cannot be caught by the cut-off line $34_{i+3}$ and cannot be reflected in the prior-art CPR image (see the right view in FIG. 4).

As described above, since each of the cut-off lines $34_i$ is in parallel with each other in the prior-art CPR image, there is a concern that there are many portions of interest 40 that cannot be caught by the cut-off line $34_i$.

Then, in the medical image processing apparatus 10 according to this embodiment, the rotation angle in the tubular cross-section $32i$ of the cut-off line $34i$ is not fixed but a CPR image in which the rotation angle around the core line 31 of the cut-off line 34 is twisted (a twisted curved multi-planner reconstruction image or hereinafter referred to as a twisted-CPR image or a tCPR image) is generated so that a first cut-off line 42 is obtained for the section of interest 41.

Therefore, first, the core-line extracting function 22 extracts the core line 31 of the tubular structure 30 on the basis of the volume data. For example, the core-line extracting function 22 first applies threshold-value processing to the volume data so as to extract a region of the tubular structure 30 included in the volume data. Then, the core-line extracting function 22 extracts the core line 31 by applying thinning processing to this region, for example.

The tubular structure 30 may be extracted full-automatically by execution of the threshold-value processing of the volume data or may be extracted such that a reconstruction image obtained from the modality 101 is displayed on the display 12 so that the user manually sets a region through the input circuit 11 while checking the reconstruction image displayed on this display 12. Moreover, it may be extracted semi-automatically such that information on one point considered by the user to belong to the tubular structure 30 is received by a click operation or the like by the user through the input circuit 11 and is subjected to segmentation (region expansion) from a position of this one point.

Moreover, as the core-line extracting method of the tubular structure 30, various full-automatic core-line extracting methods have been known such as a method using distance conversion in addition to the thinning processing method, and any arbitrary one of them can be used. Moreover, it may be so configured that the reconstruction image obtained from the modality 101 is displayed on the display 12 and the user sets the core line 31 manually through the input circuit 11 while checking the reconstruction image displayed on this display 12, for example. In this case, the core-line extracting function 22 receives information of the core line 31 set manually by the user. Moreover, when the core line 31 is extracted semi-automatically, the core-line extracting function 22 receives the information on a plurality of points considered by the user to belong to the core line 31 through the input circuit 11 by the user using a click operation or the like and extracts the core line 31 by automatic interpolation between the plurality of points, for example.

In the case of manual or semi-automatic extraction, the core-line extracting function 22 may omit a work of extracting a region of the tubular structure 30. Moreover, when a core-line extraction algorithm not requiring region information of the tubular structure 30 is used, too, the core-line extracting function 22 may omit the work of extracting a region of the tubular structure 30.

The portion of interest detecting function 23 sets the tubular cross-section 32 for each of the points at a predetermined interval on the core line 31. Moreover, the portion of interest detecting function 23 extracts a group of voxel data constituting each of the tubular cross-sections 32 from the volume data and extracts an outer wall and an inner wall of the tubular structure 30 on the basis of these voxel data values. Then, the portion of interest detecting function 23 acquires information of an average value, a minimum diameter, an area and the like on the basis of the extracted information of the inner wall and the outer wall and detects the portion of interest 40 such as a stricture or hypertrophy on the basis of the information.

The cut-off line setting function 24 sets a cut-off line 34 for each of the tubular cross-sections 32. Specifically, the cut-off line setting function 24 first sets a straight line in a section of interest 41 crossing the core line 31 and passing through the portion of interest 40 included in the section of interest 41 as the first cut-off line 42 for each of the sections of interest 41 crossing the core line 31 and which are tubular cross-sections 32 including the portions of interest 40.

Hereinafter, tubular cross-sections 32, which do not include the portion of interest 40 and are different from the section of interest 41, will be referred to as normal sections.

The cut-off line setting function 24 further sets the cut-off line (second cut-off line, interpolation cut-off line) 34 for one or a plurality of the tubular cross-sections 32 sandwiched between the two sections of interest 41 such that the second cut-off lines corresponding to the tubular cross-sections 32 (normal sections) sandwiched between the two sections of interest 41 interpolate a difference of a rotation angle θ around the core line 31 between the first cut-off lines 42 of the two sections of interest 41.

The image generating function 25 sets a curved plane so as to pass the cut-off line 34 (including the first cut-off line 42) set by the cut-off line setting function 24. Then, the image generating function 25 generates a reconstruction image (tCPR image (twisted CPR image)) along the set curved plane and displays it on the display 12.

Figure 5:
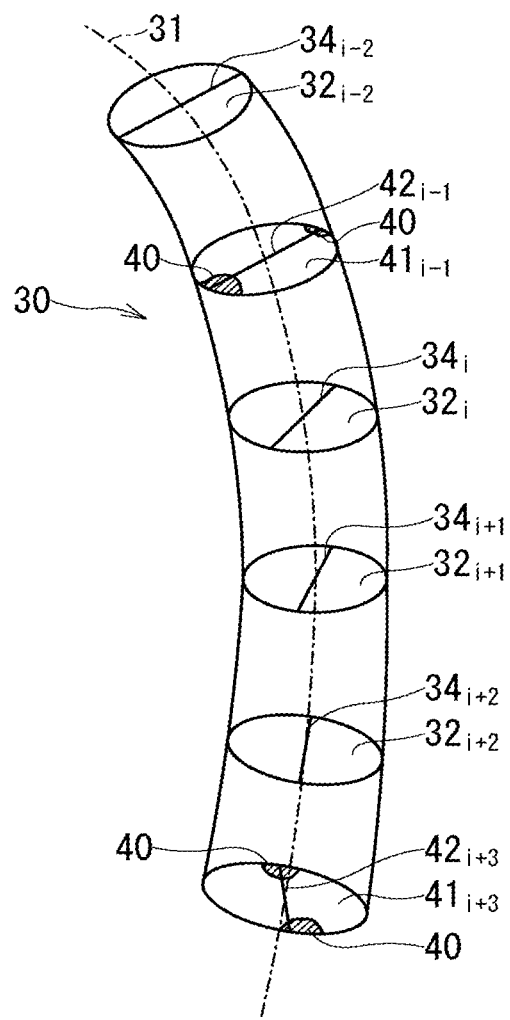
FIG. 5 is an explanatory view illustrating an example of a generating method of a tCPR image.

FIG. 5 is an explanatory view illustrating an example of a generating method of a tCPR image. As illustrated in FIG. 5, when a tCPR image is to be generated, first, the first cut-off line 42 is set for each of the sections of interest 41 by the cut-off line setting function 24. FIG. 5 illustrates, similarly to FIG. 4, an example when the tubular cross-sections $32_{i-1}$ and $32_{i+3}$ of the tubular cross-section $32_i$ are sections of interest $41_{i-1}$ and $41_{i+3}$ including the portions of interest 40, respectively.

As illustrated in FIG. 5, the first cut-off line $42_{i-1}$ and $42_{i+3}$ passing through the portion of interest 40 without fixing the rotation angle θ of the cut-off line $34_i$ in the tubular cross-section $32_i$ are set by means of the cut-off line setting function 24 for each of the sections of interest $41_{i-1}$ and $41_{i+3}$.

Moreover, as illustrated in FIG. 5, the cut-off line setting function 24 sets the cut-off lines (second cut-off lines, interpolation cut-off lines) $34_i$, $34_{i+1}$, $34_{i+2}$ so as to interpolate the difference of the rotation angles θ of the two first cut-off lines $42_{i-1}$ and $42_{i+3}$ for the tubular cross-sections $32_i$, $32_{i+1}$, $32_{i+2}$ as the normal sections sandwiched by the two sections of interest $41_{i-1}$ and $41_{i+3}$. The rotation angle θ around the core line 31 can be set by using a direction in the tubular cross-section 32 in parallel with an arbitrary predetermined plane and crossing the core line 31 as a reference (θ=0 degrees), for example. A volume rendering plane may be used as the arbitrary predetermined plane or any of major orthogonal three sections such as an axial plane and the like may be used.

Figure 6:
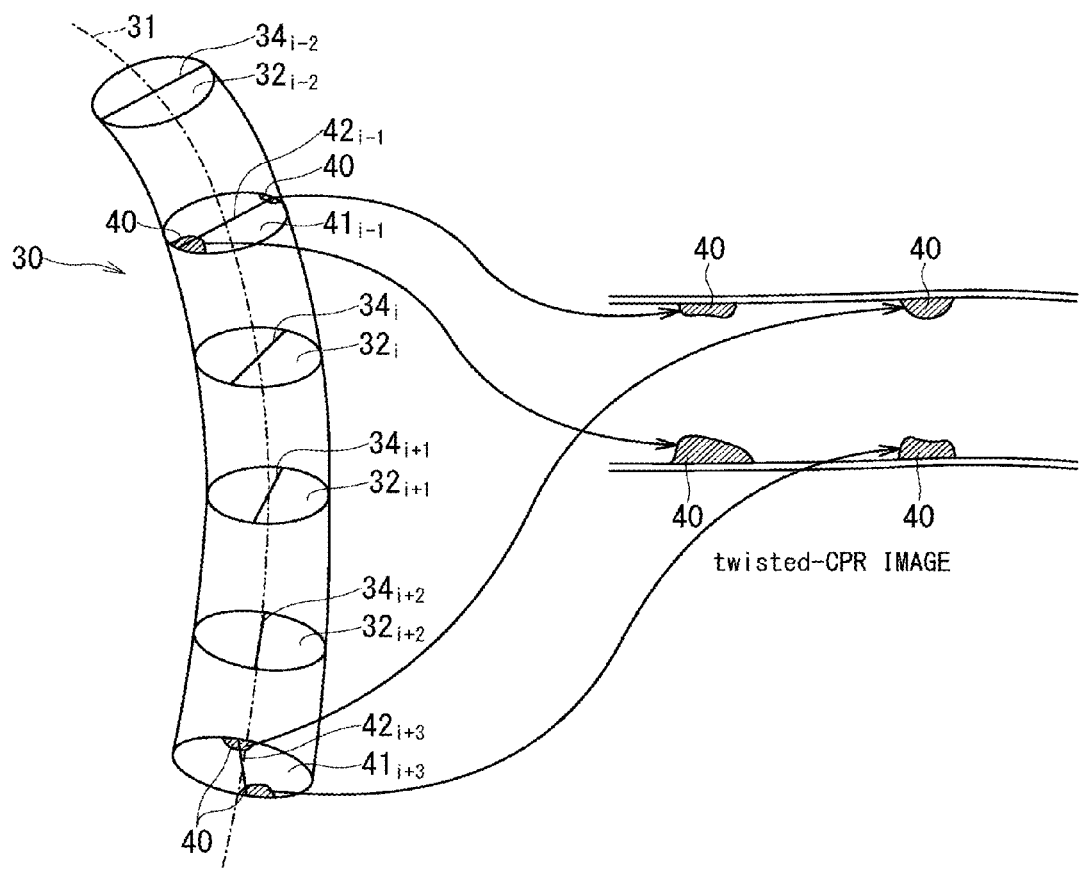
FIG. 6 is an explanatory view illustrating an example of a relation between the tCPR image and the cut-off line including the first cut-off line.

FIG. 6 is an explanatory view illustrating an example of a relation between the tCPR image and the cut-off line 34 (including the first cut-off line 42).

As illustrated in FIG. 6, the image generating function 25 generates the tCPR image (twisted CPR image) so as to pass through the cut-off line 34 (including the first cut-off line 42) set by the cut-off line setting function 24. Thus, the tCPR image can include extremely many images of the portions of interest 40 as compared with the prior-art CPR images.

Figure 7:
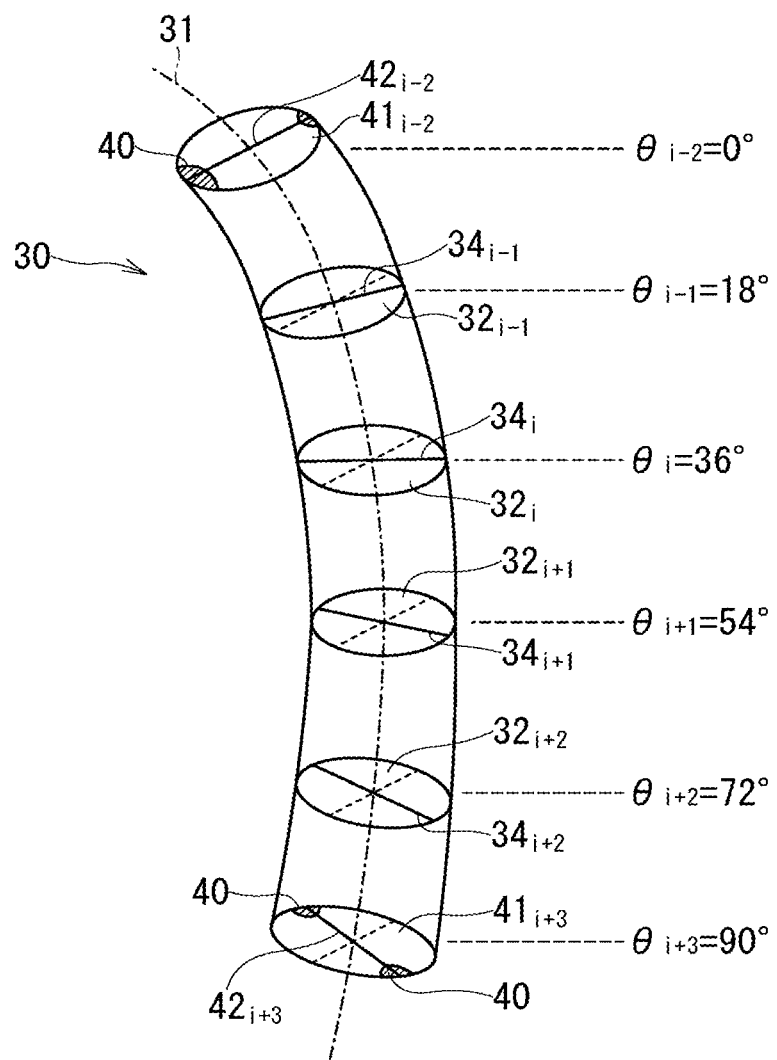
FIG. 7 is an explanatory view illustrating an example of a setting method of the cut-off line of the tubular cross-section sandwiched between the two sections of interest.

FIG. 7 is an explanatory view illustrating an example of a setting method of the cut-off line 34 of the tubular cross-section 32 sandwiched between the two sections of interest 41. FIG. 7 illustrates an example in which, assuming the rotation angle θ of the first cut-off line $42_{i-1}$ of the section of interest $41_{i-1}$ is θ=0 degrees, the rotation angle θ of the first cut-off line $42_{i+3}$ of the section of interest $41_{i+3}$ is θ=90 degrees.

As in the example illustrated in FIG. 7, regarding the cut-off lines 34 of one or a plurality of the tubular cross-sections 32 sandwiched between the two sections of interest 41, the cut-off line (second cut-off line, interpolation cut-off line) 34 is set so as to interpolate the difference of the rotation angles θ of the two first cut-off lines 42. As a result, in the tCPR image generated by twisting without fixing the rotation angle θ, too, continuity of an inner wall image or an outer wall image can be maintained.

In view of this continuity, a threshold value may be provided for the difference of the rotation angles θ between the adjacent tubular cross-sections 32. For example, if the difference of the rotation angles θ is large regardless of a short distance, the rotation angle θ is so twisted that continuity of the inner wall image or the outer wall image cannot be maintained between the two sections of interest 41 in some cases. Thus, if the difference of the rotation angles θ between the neighboring tubular cross-sections 32 would exceed the threshold value θth due to interpolation, it is preferable that the difference falls within the threshold value θth.

For example, if the threshold value θth=15 degrees in the example illustrated in FIG. 7, values of $θ_{i-1}$, $θ_i$, $θ_{i+1}$, and $θ_{i+2}$, are set to 15 degrees, 30 degrees, 45 degrees, and 60 degrees, respectively. Moreover, at this time, regarding the first cut-off line $42_{i+3}$ of the section of interest $41_{i+3}$, $θ_{i+3}$ may stay at 90 degrees or may be set to 75 degrees from the relation with $θ_{i+2}$. If it stays at 90 degrees, though continuity of the inner wall image and the outer wall image might be somewhat damaged in some cases, the images of the portions of interest 40 can be reliably included in the tCPR image. On the other hand, if it is set to 75 degrees, though the image of the portion of interest 40 displayed in the tCPR image can be small in some cases, continuity of the inner wall image and the outer wall image can be maintained.

Moreover, in order to handle a case in which a distance between the adjacent tubular cross-sections 32 is variable, this angle threshold value θth is preferably determined in accordance with a distance between the adjacent tubular cross-sections 32.

Figure 8:
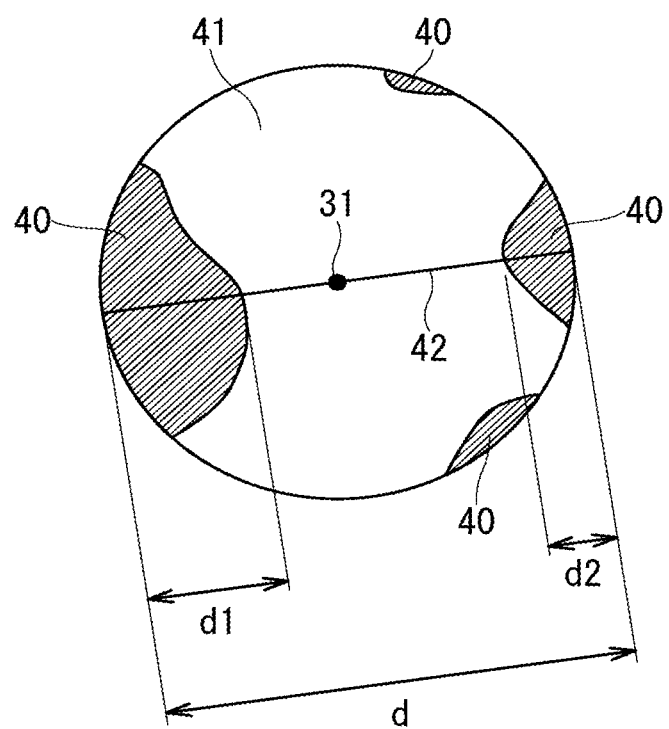
FIG. 8 is an explanatory view illustrating an example of a setting method of the first cut-off line.

FIG. 8 is an explanatory view illustrating an example of a setting method of the first cut-off line 42.

The cut-off line setting function 24 sets the first cut-off line 42 so that it passes through the portion of interest 40 and crosses the core line 31 for the section of interest 41. At this time, the cut-off line setting function 24 preferably sets the first cut-off line 42 such that the length of the first cut-off line 42 overlapping one or a plurality of portions of interest 40 is maximized. For instance, the cut-off line setting function 24 may set a straight line having a longest total of distances overlapping the portion of interest 40 (d1+d2 in an example illustrated in FIG. 8) from straight lines in the section of interest 41 crossing the core line 31 as illustrated in FIG. 8 as the first cut-off line 42.

That is, the cut-off line setting function 24 can automatically set the first cut-off line 42, the second cut-off line, the interpolation cut-off line and other cut-off lines 34 on the basis of the information of the portion of interest 40 detected by the portion of interest detecting function 23. Therefore, the image generating function 25 can automatically generate the tCPR image (twisted CPR image) and display it on the display 12 so that it passes through the cut-off line 34 (including the first cut-off line 42) set by the cut-off line setting function 24.

Moreover, the tCPR image may be generated semi-automatically, and in this case, the cut-off line setting function 24 receives setting of the cut-off line 34 at a predetermined position through the input circuit 11 by the user. For example, if the first cut-off line 42 is set to two portions of interest 40 through the input circuit 11 by the user, the cut-off line setting function 24 automatically sets the cut-off line 34 between these two first cut-off lines 42. Moreover, if there is the portion of interest 40 between these two first cut-off lines 42, the cut-off line setting function 24 automatically sets the first cut-off line 42 passing through this portion of interest 40. Moreover, the first cut-off line 42 passing through all the portions of interest 40 may be set manually by the user.

Moreover, even if the cut-off line 34 set by the user is received, when the difference of the rotation angles θ between the adjacent tubular cross-sections 32 exceeds the threshold value θth if interpolation is executed, the cut-off line setting function 24 may change the setting of the cut-off line 34 set by the user so that it is contained within the threshold value θth.

Moreover, even after the tCPR image based on the cut-off line 34 set full-automatically or semi-automatically is generated and displayed on the display 12, when the cut-off line setting function 24 receives a change instruction by the user through the input circuit 11, the cut-off line setting function 24 changes setting of the cut-off line 34 such as a position, a rotation angle and the like in accordance with this change instruction. In this case, the image generating function 25 generates the tCPR image and displays it on the display 12 on the basis of the cut-off line 34 after the change. At this time, the tCPR image may be displayed in parallel with the tCPR image based on the cut-off line 34 before the change.

Figure 9A:
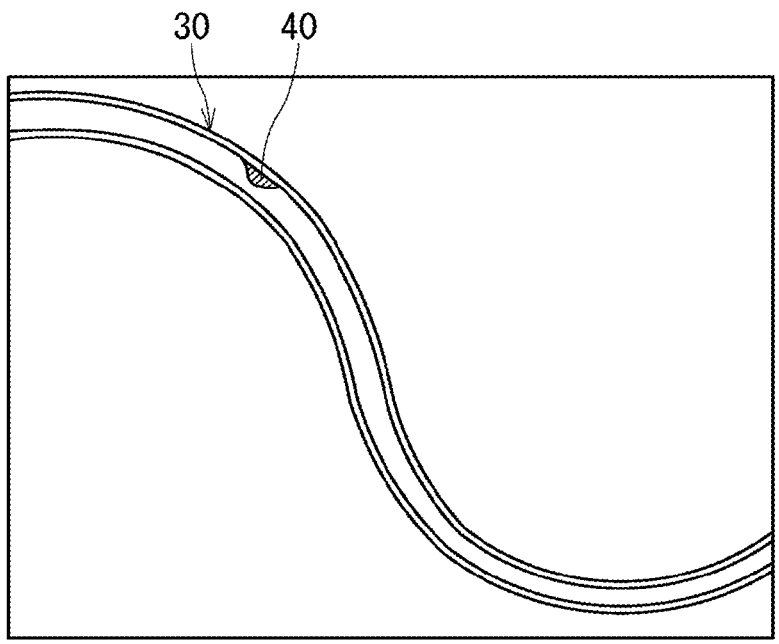
FIG. 9A is an explanatory view illustrating an example of the prior-art CPR image.
Figure 9B:
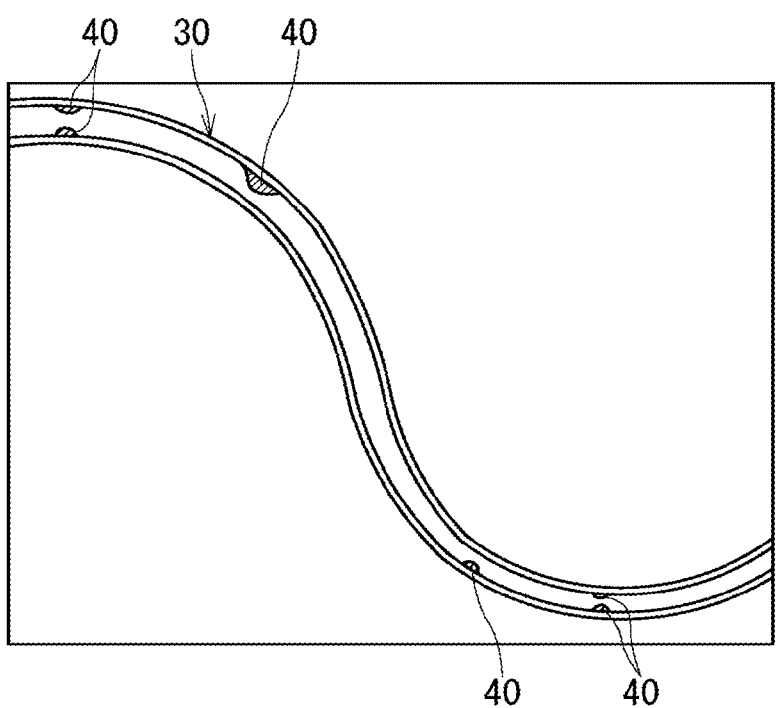
FIG. 9B is an explanatory view illustrating an example of the tCPR image.

FIG. 9A is an explanatory view illustrating an example of the prior-art CPR image and FIG. 9B is an explanatory view illustrating an example of the tCPR image.

As illustrated in FIGS. 9A and 9B, the tCPR image can include more information on the portion of interest 40 than the prior-art CPR image. When the tCPR image as illustrated in FIGS. 9A and 9B is to be displayed, the image generating function 25 may superpose/display a highlighted image indicating a position of the portion of interest 40 on the tCPR image. For the highlighted image, figures or character information surrounding the portion of interest, use of different colors or brightness for figures surrounding the portion of interest according to an abnormality level or a combination of them can be used.

Subsequently, a calculating method of a fractional flow reserve based on the tCPR image will be described.

Figure 10:
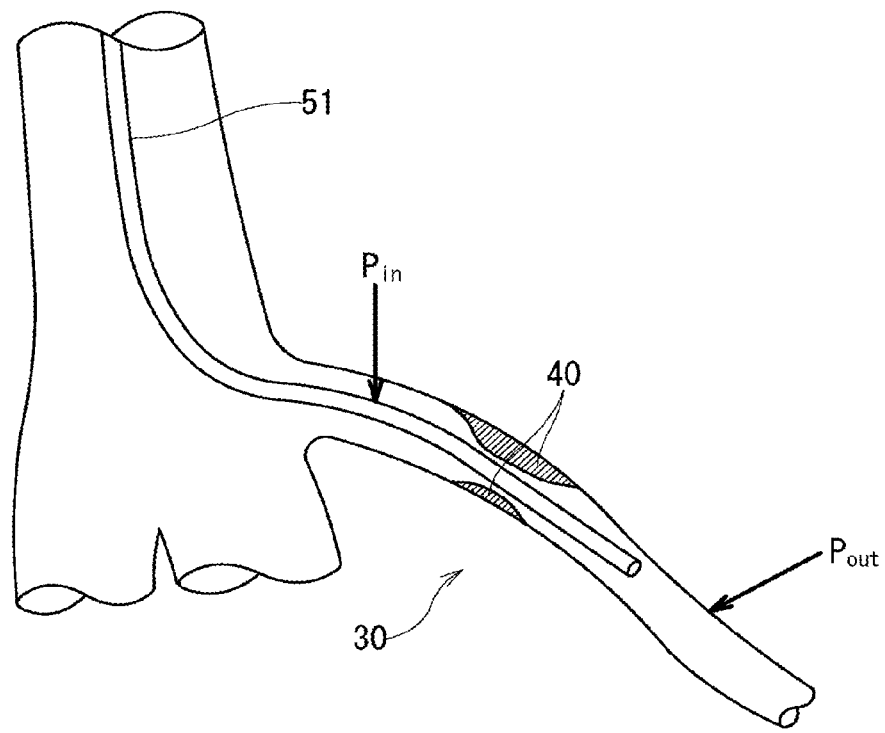
FIG. 10 is a view for explaining FFR (Fractional Flow Reserve)

FIG. 10 is a view for explaining FFR (Fractional Flow Reserve).

The FFR is used by a doctor as an index for selecting whether a catheter operation is to be done or a pharmacotherapy is to be given. For evaluation of a degree of progress of abnormality such as a stricture at the portion of interest 40, a pressure in the tubular structure 30 is used. Specifically, a pressure wire 51 such as a catheter is directly inserted into the tubular structure 30, and Pin which is a pressure on a front part of the portion of interest 40 and Pout which is a pressure of a rear part are measured. A value of the FFR is defined as FFR=Pout/Pin. The value of this FFR is used as a determination index such that if FFR is lower than 0.8, a catheter operation is conducted, for example, while if it is larger than 0.8, it is handled by a pharmacotherapy.

However, the FFR measurement using the pressure wire 51 is invasive and applies a large load to an object. Thus, in recent years, a simulation-based FFR calculating method using a fluid analysis has been developed.

One of this type of FFR calculation method is a CFD (Computational Fluid Dynamics) calculation method. The CFD calculation method is a method of acquiring a value of FFR by using Navier-Stokes equation with physical parameters such as a shape of the tubular structure 30, viscosity of a fluid flowing inside the tubular structure 30 and the like as inputs.

This CFD calculation method requires long time for calculation if the shape of the tubular structure 30 is 3D. On the other hand, the tCPR image generated by the medical image processing apparatus 10 according to this embodiment is a sectional image of the tubular structure 30, that is, a 2D image and also an image which includes an extremely large amount of information of the portion of interest 40 as compared with the prior-art CPR image. Therefore, by making a 2D CFD calculation by using shape information of the tCPR image, accurate FFR reflecting more information of the portion of interest 40 than a case of using the prior-art CPR image can be acquired in a shorter time and with a lighter load than a 3D CFD calculation.

The index calculating function 26 of the processing circuitry 15 makes the 2D CDF calculation on the basis of the shape information of the tCPR image of the tubular structure 30 generated by the image generating function 25 so as to acquire the FFR. By using the shape information of the tCPR image, more information on the portion of interest 40 can be reflected than the case of using the shape information of the prior-art CPR image and thus, more accurate FFR can be acquired.

Figure 11:
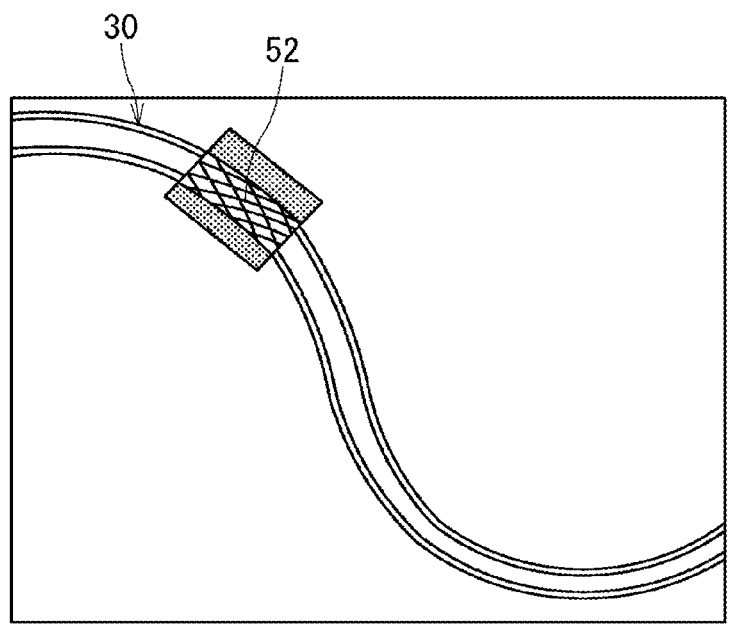
FIG. 11 is an explanatory view illustrating an example of the tCPR image when a simulation of insertion of an implant is performed.

FIG. 11 is an explanatory view illustrating an example of the tCPR image when a simulation of insertion of an implant 52 is performed.

If insertion of the implant 52 such as a stent is scheduled and if the shape information of mesh data (polygon data and the like) of the implant 52 can be obtained, insertion can be simulated by superposing/displaying an image of the implant 52 on the basis of the shape information of the implant 52 on the tCPR image. Moreover, if the shape information of the mesh data (polygon data and the like) of the implant 52 can be obtained, virtual FFR when the implant 52 is inserted can be acquired by making the 2D CFD calculation reflecting the shape information when the implant 52 is inserted with respect to the shape information of the tubular structure 30.

The shape information of the implant 52 may be stored in the memory circuitry 14 in advance, may be downloaded from the network 100 or may be set by the user through the input circuit 11.

Figure 12:
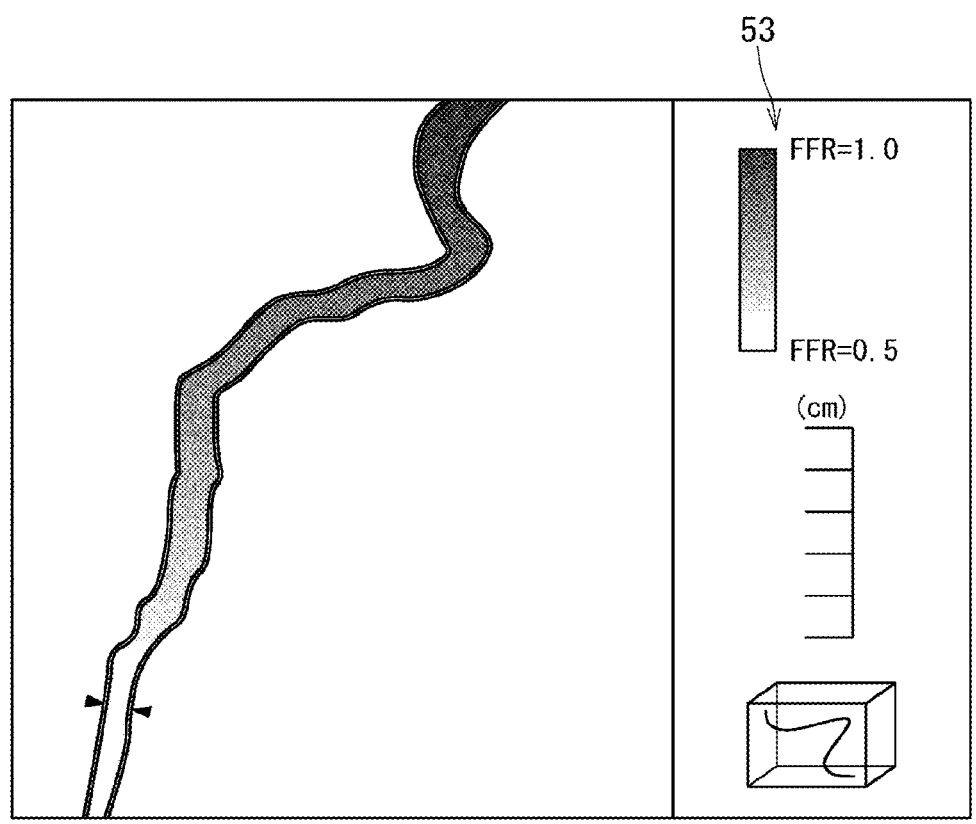
FIG. 12 is an explanatory view illustrating an example of a state in which the FFR is superposed on the tCPR image.

FIG. 12 is an explanatory view illustrating an example of a state in which the FFR is superposed on the tCPR image.

An image indicating the information of the FFR calculated by the index calculating function 26 may be superposed on the tCPR image of the tubular structure 30 as illustrated in FIG. 12. At this time, the image indicating the information of the FFR may be an image expressing an FFR value by using contrast, brightness or colors, for example, and in this case, a color bar 53 for associating the contrast, the brightness or the colors with the FFR value is preferably further displayed as illustrated in FIG. 12.

Subsequently, an example of an operation of the medical image processing apparatus and the medical image processing method according to this embodiment will be described.

Figure 13:
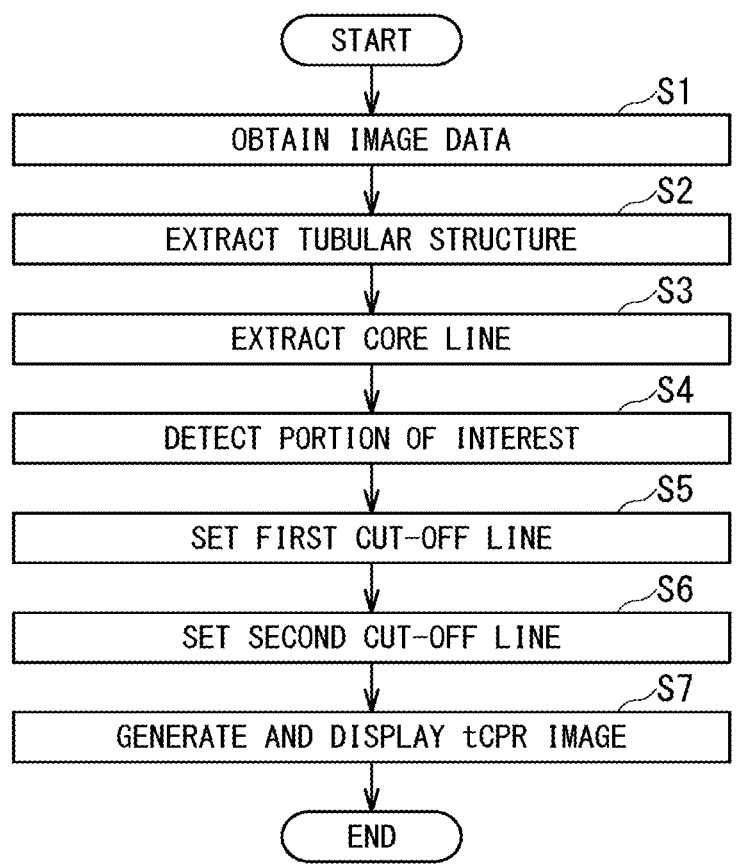
FIG. 13 is a flowchart illustrating a procedure when the tCPR image including more images on portions of interest is generated by a processor of the processing circuitry.

FIG. 13 is a flowchart illustrating a procedure when the tCPR image including more images on portions of interest is generated by a processor of the processing circuitry 15. In FIG. 13, reference numerals of the character S and numbers indicate each step in the flowchart.

First, at Step S1, the image data obtaining function 21 obtains at least volume data generated by the modality 101 and stores it in the memory circuitry 14.

Subsequently, at Step S2, the core-line extracting function 22 extracts a region of the tubular structure 30 included in the volume data full-automatically by applying threshold value processing to the volume data, manually or semi-automatically.

Subsequently, at Step S3, the core-line extracting function 22 extracts the core line 31 full-automatically by applying thinning processing to this area, for example, manually or semi-automatically.

If the core line 31 is extracted manually or semi-automatically at Step S3 or if the core line 31 is extracted by using a core-line extraction algorithm not requiring region information of the tubular structure 30, Step S2 may be omitted.

Subsequently, at Step S4, the portion of interest detecting function 23 detects the portion of interest 40 such as a stricture or hypertrophy for each of the tubular cross-sections 32. Specifically, the portion of interest detecting function 23 sets the tubular cross-section 32 for each of points at a predetermined interval on the core line 31, extracts a group of voxel data constituting each of the tubular cross-sections 32 and extracts the outer wall and the inner wall of the tubular structure 30 on the basis of these voxel data values. Then, the portion of interest detecting function 23 acquires information such as an average value, a minimum diameter, an area and the like on the basis of the extracted information of the inner wall and the outer wall and detects the portion of interest 40 such as a stricture or hypertrophy on the basis of the information.

Subsequently, at Step S5, the cut-off line setting function 24 sets a straight line in the section of interest 41 crossing the core line 31 and passing through the portion of interest 40 included in the section of interest 41 full-automatically, manually or semi-automatically as the first cut-off line 42 for each of the sections of interest 41 which are tubular cross-sections 32 crossing the core line 31 and also including the portion of interest 40.

At Step S5, if all the first cut-off lines 42 are set manually, Step S4 may be omitted.

Subsequently, at Step S6, the cut-off line setting function 24 sets the cut-off line (second cut-off line, interpolation cut-off line) 34 so as to interpolate the difference of the rotation angles θ around the core line 31 of the first cut-off line 42 of each of the two sections of interest 41 for the one or a plurality of tubular cross-sections 32, sandwiched by the two sections of interest 41, of the tubular cross-sections (normal sections) 32 not including the portion of interest 40.

Subsequently, at Step S7, the image generating function 25 sets a curved plane so as to pass through the cut-off line 34 (including the first cut-off line 42) set by the cut-off line setting function 24, generates a reconstruction image (tCPR image (twisted CPR image)) along the set curved plane and displays it on the display 12.

By means of the aforementioned procedure, the tCPR image including more images of portions of interest can be generated.

Figure 14:
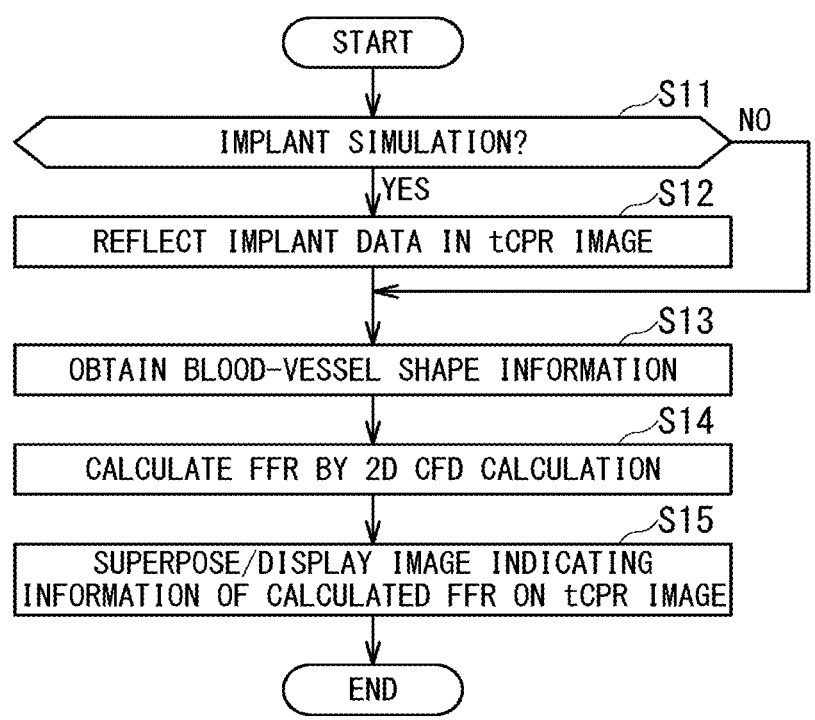
FIG. 14 is a flowchart illustrating a procedure when the FFR is calculated by the processor of the processing circuitry on the basis of the shape information of the tCPR image.

FIG. 14 is a flowchart illustrating a procedure when the FFR is calculated by the processor of the processing circuitry 15 on the basis of the shape information of the tCPR image.

In FIG. 14, reference numerals of the character S and numbers indicate each step in the flowchart.

This procedure is started when the tCPR image of the tubular structure 30 is generated by the image generating function 25.

First, at Step S11, the image generating function 25 determines whether or not simulation of a case of insertion of the implant 52 is performed. The execution instruction of this simulation is given to the image generating function 25 by the user through the input circuit 11, for example. If insertion simulation of the implant 52 is performed, routine proceeds to Step S12. On the other hand, if the insertion simulation of the implant 52 is not performed, the routine proceeds to Step S13.

Subsequently, at Step S12, the image generating function 25 reflects the shape information of the implant 52 in the tCPR image.

Subsequently, at Step S13, the index calculating function 26 obtains the shape information of the tCPR image of the tubular structure 30 generated by the image generating function 25.

Subsequently, at Step S14, the index calculating function 26 acquires FFR by making the 2D CFD calculation on the basis of the shape information of the tCPR image of the tubular structure 30 generated by the image generating function 25. At this time, if the shape information of the implant 52 is reflected in the tCPR image at Step 512, virtual FFR of a case of insertion of the implant 52 is acquired at this Step S14.

Subsequently, at Step S15, the image generating function 25 superposes/displays the image indicating the FFR information on the tCPR image of the tubular structure 30.

By means of the aforementioned procedure, the FFR can be calculated on the basis of the shape information of the tCPR image.

The image generating function 25 may generate an image like a stretch CPR (twisted SPR image) stretched along the core line 31 similarly to the tCPR image.

Moreover, the portion of interest detecting function 23 may sort the portions of interest 40 to soft plaque and hard plaque and in this case, the image generating function 25 may display the tCPR images of the soft plaque and the hard plaque in modes different from each other. Moreover, in this case, the cut-off line setting function 24 may set the first cut-off line 42 using only the soft plaque as the portion of interest 40.

The medical image processing apparatus 10 according to this embodiment can set the first cut-off line 42 so as to pass through the portion of interest 40 for each of the sections of interest 41, which are tubular cross-sections 32 including the portion of interest 40, included in the sections crossing the core line 31 of the tubular structure 30, and then can generate the tCPR image as the section of the tubular structure 30 passing through this first cut-off line 42. Thus, this tCPR image can be considered to be an accurate image including information of more portions of interest 40 than the prior-art CPR image.

Therefore, in order to grasp all the portions of interest 40 in the prior-art CPR image, the CPR image needs to be generated on various sections along the core line 31, while according to the tCPR image generated by the medical image processing apparatus 10 according to this embodiment, the user can check all the portions of interest 40 in the one tCPR image, whereby possibility of overlooking the portion of interest 40 can be drastically lowered.

Moreover, regarding the cut-off line 34 of the one or a plurality of tubular cross-sections 32 sandwiched between the two sections of interest 41, the cut-off line (second cut-off line, interpolation cut-off line) 34 is set so as to interpolate the difference of rotation angles θ of the two first cut-off lines 42. As a result, in the tCPR image generated by twisting but not fixing the rotation angle θ, too, continuity of the inner wall image or the outer wall image can be maintained, and a sense of discomfort given to the user can be alleviated.

Moreover, the medical image processing apparatus 10 according to this embodiment can acquire FFR by making the 2D CFD calculation by using the shape information of this tCPR image. Thus, an accurate FFR reflecting the information of the more portions of interest 40 than using the prior-art CPR image can be acquired in a shorter time and with a lighter load than a 3D CFD calculation.

With at least one of the above-described embodiments, the medical image processing apparatus 10 can set the first cut-off line 42 so as to pass through the portion of interest 40 for each of the sections of interest 41 which are tubular cross-sections 32 including the portion of interest 40 in the sections crossing the core line 31 of the tubular structure 30, and can generate the tCPR image as the section of the tubular structure 30 passing through this first cut-off line 42. Thus, a twisted curved multi-planner reconstruction image (tCPR image) including more images of portions of interest can be generated.

The processing circuitry in the above-described embodiments is an example of the processing circuitry described in the claims. In addition, the term "processor" used in the explanation in the above-described embodiments, for instance, a circuit such as a dedicated or general-purpose CPU (Central Processing Unit), a dedicated or general-purpose GPU (Graphics Processing Unit), an ASIC (Application Specific Integrated Circuit), a programmable logic device including an SPLD (Simple Programmable Logic Device) and a CPLD (Complex Programmable Logic Device) as examples, and an FPGA (Field Programmable Gate Array). A processor implements various types of functions by reading out programs stored in the memory circuit and executing the programs.

In addition, programs may be directly installed in the circuit of a processor instead of storing programs in the memory circuit. In this case, the processor implements various types of functions by reading out programs stored in its own circuit and executing the programs. Moreover, each function of the processing circuitry may be implemented by processing circuitry configured of a single processor. Further, the processing circuitry may be configured by combining plural processors independent of each other so that each function of the processing circuitry is implemented by causing each processor to execute the corresponding program. When plural processors are provided for the processing circuitry, a memory circuit for storing the programs may be provided for each processor or one memory circuit may collectively store all the programs corresponding to all the processors.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

Further, although an example of processing the steps of the flowchart is described in the embodiments in which each steps are time-sequentially performed in order along the flowchart, each step of the flowchart may not be necessarily processed in a time series, and may be executed in parallel or individually executed.

The invention claimed is:

1. A medical image processing apparatus, comprising processing circuitry configured to:
    extract a core line of a tubular structure from three dimensional medical image data;
    for each section of interest of a plurality of sections of interest, the section of interest crossing the core line, being a tubular cross-section of the tubular structure, and including a portion of interest, set a straight line in the section of interest crossing the core line and passing through the portion of interest included in the section of interest as a first cut-off line;
    set a curved plane such that the curved plane passes through a plurality of first cut-off lines being set in the corresponding plurality of sections of interest; and
    generate a reconstruction image along the set curved plane.

2. The medical image processing apparatus according to claim 1, wherein the processing circuitry:
    for at least one different section, each of the at least one different section being different from the section of interest, crossing the core line, and being a tubular cross-section of the tubular structure, sets a straight line in each of the at least one different section crossing the core line as a second cut-off line; and
    sets the curved plane so as to pass through the plurality of first cut-off lines and the second cut-off line.

3. The medical image processing apparatus according to claim 2, wherein the processing circuitry sets, for one or a plurality of different sections sandwiched between two of the sections of interest, the second cut-off line such that the second cut-off line interpolates a difference of rotation angles around the core line between two first cut-off lines corresponding to the two of the sections of interest.

4. The medical image processing apparatus according to claim 1, wherein, when a plurality of portions of interest are included in the section of interest, the processing circuitry sets the first cut-off line such that the length of the first cut-off line overlapping one or a plurality of portions of interest is maximized.

5. The medical image processing apparatus according to claim 3, wherein, for the one or the plurality of different sections sandwiched between the two of the sections of interest, the processing circuitry sets the second cut-off line such that a difference of rotation angles around the core line between two second cut-off lines falls within a threshold value, the two second cut-off lines being corresponding to neighboring different sections of the one or the plurality of different sections sandwiched between the two of the sections of interest.

6. The medical image processing apparatus according to claim 1, wherein the processing circuitry acquires fractional flow reserve by performing 2D CFD calculation based on information on a blood-vessel shape obtained from the reconstruction image.

7. The medical image processing apparatus according to claim 6, wherein the processing circuitry acquires virtual fractional flow reserve for simulating an insertion of an implant member by performing 2D CFD calculation based on the information on blood-vessel shape and information on a shape of the implant member to be inserted into the tubular structure.

8. The medical image processing apparatus according to claim 6, wherein the processing circuitry superimposes an image indicating information of the fractional flow reserve on the reconstruction image.

9. The medical image processing apparatus according to claim 1, wherein the processing circuitry is configured so as to be manually settable of the first cut-off line in accordance with an instruction by a user through an input circuit.

10. A medical image processing method comprising:
    extracting a core line of a tubular structure from three dimensional medical image data;
    for each section of interest of a plurality of sections of interest, the section of interest crossing the core line, being a tubular cross-section of the tubular structure, and including a portion of interest, setting a straight line in the section of interest crossing the core line and passing through the portion of interest included in the section of interest as a first cut-off line;
    setting a curved plane such that the curved plane passes through a plurality of first cut-off lines being set in the corresponding plurality of sections of interest; and
    generating a reconstruction image along the set curved plane.

* * * * *